United States Patent
Char et al.

(10) Patent No.: US 10,117,830 B2
(45) Date of Patent: *Nov. 6, 2018

(54) STABLE PARENTERAL DNJ COMPOSITIONS

(71) Applicant: Amicus Therapeutics, Inc., Cranbury, NJ (US)

(72) Inventors: Hing Char, East Brunswick, NJ (US); Sergey Tesler, Monroe, NJ (US); Jiping Yang, Bridgewater, NJ (US); Enrique Dilone, Basking Ridge, NJ (US)

(73) Assignee: Amicus Therapeutics, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/822,655

(22) Filed: Nov. 27, 2017

(65) Prior Publication Data

US 2018/0078497 A1 Mar. 22, 2018

Related U.S. Application Data

(63) Continuation of application No. 14/759,770, filed as application No. PCT/US2014/010891 on Jan. 9, 2014, now Pat. No. 9,827,189.

(60) Provisional application No. 61/914,839, filed on Dec. 11, 2013, provisional application No. 61/750,677, filed on Jan. 9, 2013.

(51) Int. Cl.
| | | |
|---|---|---|
| *A61K 31/445* | (2006.01) | |
| *A61K 31/45* | (2006.01) | |
| *A61K 47/02* | (2006.01) | |
| *A61K 47/12* | (2006.01) | |
| *A61K 9/00* | (2006.01) | |
| *A61K 47/18* | (2017.01) | |

(52) U.S. Cl.
CPC .......... *A61K 9/0019* (2013.01); *A61K 31/445* (2013.01); *A61K 31/45* (2013.01); *A61K 47/02* (2013.01); *A61K 47/12* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 5,786,368 A | 7/1998 | Platt et al. | |
| 9,827,189 B2 * | 11/2017 | Char | A61K 31/445 |
| 2006/0264467 A1 | 11/2006 | Mugrage et al. | |
| 2010/0119502 A1 * | 5/2010 | Do | A61K 38/47 424/94.61 |

FOREIGN PATENT DOCUMENTS

| | | |
|---|---|---|
| WO | 2011/103114 A1 | 8/2011 |
| WO | 2011/131926 A1 | 10/2011 |

* cited by examiner

*Primary Examiner* — Michael Barker
(74) *Attorney, Agent, or Firm* — Servilla Whitney LLC

(57) ABSTRACT

A stable pharmaceutical composition that includes an active agent selected from 1-deoxynojirimycin, a pharmaceutically acceptable salt thereof, or a derivative thereof, and a buffer, wherein the stable pharmaceutical composition is capable of being parenterally administered to a human without deleterious health effects. Pompe disease is an example of a lysosomal storage disorder. Pompe disease is caused by a deficiency in the enzyme acid alpha-glucosidase (GAA). GAA metabolizes glycogen, a storage form of sugar used for energy, into glucose.

20 Claims, 5 Drawing Sheets

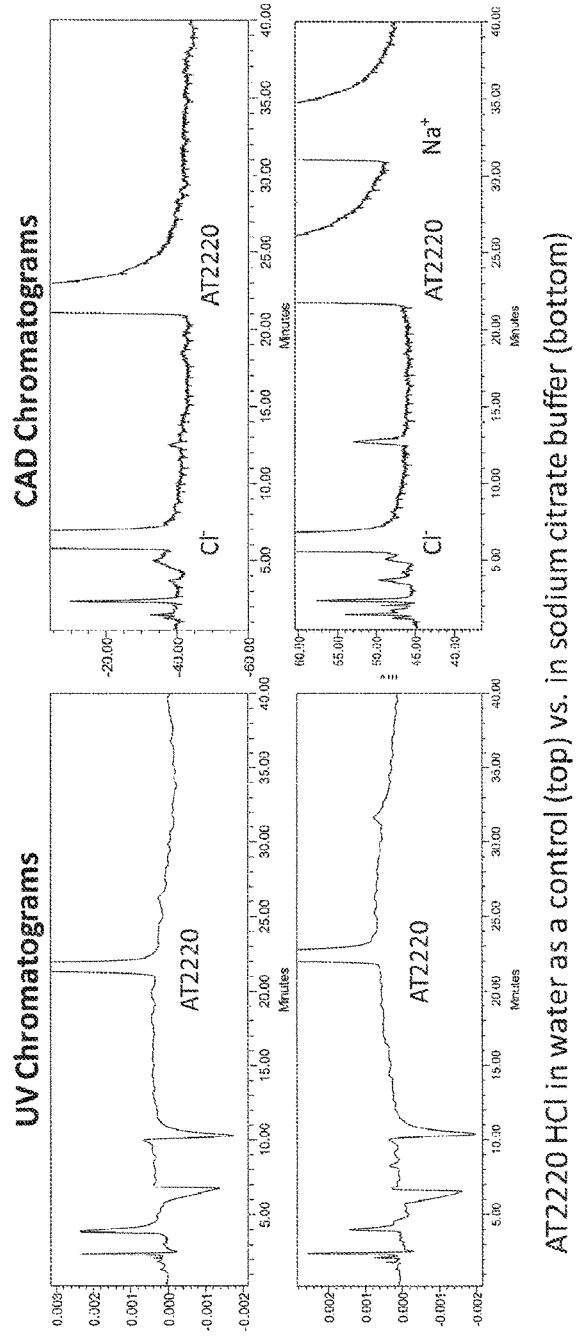

STABLE PARENTERAL DNJ COMPOSITIONS

REFERENCE TO RELATED APPLICATIONS

The present application is a continuation of U.S. application Ser. No. 14/759,770, which is the National Phase entry of PCT/US14/10891, filed Jan. 9, 2014, claims the benefit of U.S. Provisional Application No. 61/750,677, filed Jan. 9, 2013, and U.S. Provisional Application No. 61/914,839, filed Dec. 11, 2013, each of which being hereby incorporated by reference in their entirety.

BACKGROUND

Pompe disease is an example of a lysosomal storage disorder. Pompe disease is caused by a deficiency in the enzyme acid alpha-glucosidase (GAA). GAA metabolizes glycogen, a storage form of sugar used for energy, into glucose. The accumulation of glycogen is thought to lead to progressive muscle myopathy throughout the body which affects various body tissues, particularly the heart, skeletal muscles, liver, and nervous system. According to the National Institute of Neurological Disorders and Stroke, Pompe disease is estimated to occur in about 1 in 40,000 births.

There are three recognized types of Pompe disease—infantile, juvenile, and adult onset. Infantile is the most severe, and presents with symptoms that include severe lack of muscle tone, weakness, enlarged liver and heart, and cardiomyopathy. Swallowing may become difficult and the tongue may protrude and become enlarged. Most children die from respiratory or cardiac complications before the age of two. Juvenile onset Pompe disease first presents in early to late childhood and includes progressive weakness of the respiratory muscles in the trunk, diaphragm, and lower limbs, as well as exercise intolerance. Most juvenile onset Pompe patients do not live beyond the second or third decade of life. Adult onset symptoms involve generalized muscle weakness and wasting of respiratory muscles in the trunk, lower limbs, and diaphragm. Some adult patients are devoid of major symptoms or motor limitations.

Enzyme replacement therapy (ERT) is one approach to treating Pompe Disease. One of the main complications with ERT is the attainment and maintenance of therapeutically effective amounts of enzyme due to rapid degradation of the infused enzyme. As a result, ERT requires numerous, high-dose infusions and is costly and time consuming.

A newer approach to treating Pompe Disease, a specific chaperone strategy, rescues mutated proteins from degradation presumably in the endoplasmic reticulum (ER) or in other cellular protein degradation/disposal systems. This strategy employs small molecule reversible inhibitors which specifically bind to a defective lysosomal enzyme associated with a particular lysosomal disorder. The chaperone strategy involves the use of a small molecule that facilitates the correct folding of a mutated protein, to prevent undue or abnormal degradation from the ER quality control system. These specific chaperones are designated as active site-specific chaperones. See, e.g., U.S. Pat. Nos. 6,274,597, 6,583,158, 6,589,964, and 6,599,919, each of which incorporated by reference herein. U.S. Pat. No. 6,583,158 discloses 1-deoxynojirimycin (DNJ) and other active site-specific chaperones for treating Pompe Disease.

1-DNJ can be provided in a solid form for oral administration. However, if DNJ is to be administered as part of a combination therapy along with ERT, there is a desire for parenterally administered DNJ, as a parenteral formulation allows for greater dosage control and administration access. Also, patients, expecially infants, may have difficulty swallowing oral dosage forms, regardless of whether monotherapy or combination therapy is elected as a form of treatment. Although 1-DNJ is soluble and generally stable in aqueous formulations, such formulations are not suited for parenteral administration because of the need for pH control over a practical shelf-life of the formulation and to provide a suitable osmolality for parenteral administration such that the formulation does not cause deleterious health effects.

BRIEF SUMMARY OF THE INVENTION

One aspect of the presently disclosed subject matter provides a stable pharmaceutical composition that includes an active agent selected from 1-deoxynojirimycin, a pharmaceutically acceptable salt thereof, or a derivative thereof, and a buffer, wherein the stable pharmaceutical composition is capable of being parenterally administered to a human without deleterious health effects.

The active agent can be, for example, 1-deoxynojirimycin hydrochloride or N-butyl-deoxynojirimycin, or a pharmaceutically acceptable salt thereof (e.g., N-butyl-deoxynojirimycin). In certain embodiments, the buffer can be selected from a phosphate buffer (e.g., a sodium phosphate buffer), a citrate buffer (e.g., a sodium citrate buffer), an acetate buffer (e.g., sodium acetate buffer) and a bicarbonate buffer (e.g., a sodium bicarbonate buffer). The pH of the pharmaceutical composition can be from about 4.6 to about 5.5 (e.g., 5.0). The pharmaceutical composition can be formulated for subcutaneous administration, or intravenous administration. In certain embodiments, the pharmaceutical composition demonstrate a lack of hemolytic potential.

In certain embodiments, the active agent (e.g., 1-DNJ-HCl) can be present at a concentration of from about 25 mg/mL to about 30 mg/mL and the buffer is present at a concentration of from about 40 mM to about 50 mM. In certain embodiments, the active agent (e.g., 1-DNJ) can be present at a concentration of about 25 mg/mL or about 30 mg/mL and the buffer is present at a concentration of about 40 mM or 50 mM. The total amount of active agent can be, for example, 300 mg and the total volume of the composition can be, for example, about 10.5 mL.

In certain embodiments, the pharmaceutical composition can further include a chelating agent (e.g., EDTA). For example, the active agent can be present at a concentration of about 30 mg/mL, the buffer can be present at a concentration of about 50 mM, and EDTA can be present at a concentration of about 0.05% weight by volume. In one embodiment, the active agent can be present at a concentration of about 25 mg/mL, the buffer can be present at a concentration of about 50 mM, and EDTA can be present at a concentration of about 0.05% weight by volume.

In certain embodiments, the composition can be shelf-stable for at least about one year under a nitrogen atmosphere and a temperature of from about 2° C. to about 42° C. In one embodiment, the composition can be shelf-stable for at least about one year under a nitrogen atmosphere and a temperature of from about 2° C. to about 8° C. In another embodiment, the composition can be shelf-stable for at least about one year under a nitrogen atmosphere and a temperature of from about 23° C. to about 27° C. In another embodiment, the composition can be shelf-stable for at least about one year under a nitrogen atmosphere and a temperature of from about 38° C. to about 42° C.

In one embodiment, the composition can be shelf-stable for at least about one year under the air atmosphere or a combination of air and nitrogen atmosphere and a temperature of from about 2° C. to about 8° C. In another embodiment, the composition can be shelf-stable for at least about one year under the air atmosphere or a combination of air and nitrogen atmosphere and a temperature of from about 23° C. to about 27° C. In another embodiment, the composition can be shelf-stable for at least about one year under the air atmosphere or a combination of air and nitrogen atmosphere and a temperature of from about 38° C. to about 42° C.

A second aspect of the presently disclosed subject matter provides a method for increasing the stability of an active agent selected from 1-deoxynojirimycin, a pharmaceutically acceptable salt thereof, or a derivative thereof in a formulation for a parenteral administration to a human, that includes introducing a buffer to the active agent to prepare the formulation and storing the formulation under the nitrogen atmosphere or under the air atmosphere or a combination of air and nitrogen atmosphere and a temperature from about 2° C. to about 42° C. In some embodiments the atmosphere is a nitrogen atmosphere. In some embodiments the temperature is below room temperature (e.g., from about 2° C. to about 8° C.). In some embodiments the temperature is from about 23° C. to about 27° C. In some embodiments the temperature is from about 38° C. to about 42° C. The formulation can be shelf-stable for at least one year, or at least two years.

Another aspect of the presently disclosed subject matter provides a kit for parenteral administration to a human of a stable pharmaceutical composition that includes an active agent selected from 1-deoxynojirimycin, a pharmaceutically acceptable salt thereof, or a derivative thereof, and a buffer, wherein the composition is shelf-stable for at least about one year under a nitrogen atmosphere or shelf-stable for at least about one year under an air atmosphere or shelf-stable for at least about one year under a combination of air and nitrogen atmosphere and a temperature of from about 2° C. to about 42° C. In some embodiments the atmosphere, for which the formulation is stable, is a nitrogen atmosphere. In some embodiments the temperature, for which the formulation is stable is below room temperature (e.g., from about 2° C. to about 8° C.). In some embodiments the temperature, for which the formulation is stable, is from about 23° C. to about 27° C. In some embodiments the temperature, for which the formulation is stable, is from about 38° C. to about 42° C.

BRIEF DESCRIPTION OF THE DRAWINGS

FIG. 5 shows stability of 1-deoxynojirimycin chloride in sodium citrate buffer solution compared to stability in water as described in Example 6. The stability was measured by normal phase high performance liquid chromatography (NP-HPLC). The left spectra shows 1-deoxynojirimycin as detected by UV detector, while the right spectra show 1-deoxynojirimycin as detected by Charged Aerosol Detector (CAD).

DETAILED DESCRIPTION OF THE INVENTION

Figure 1:
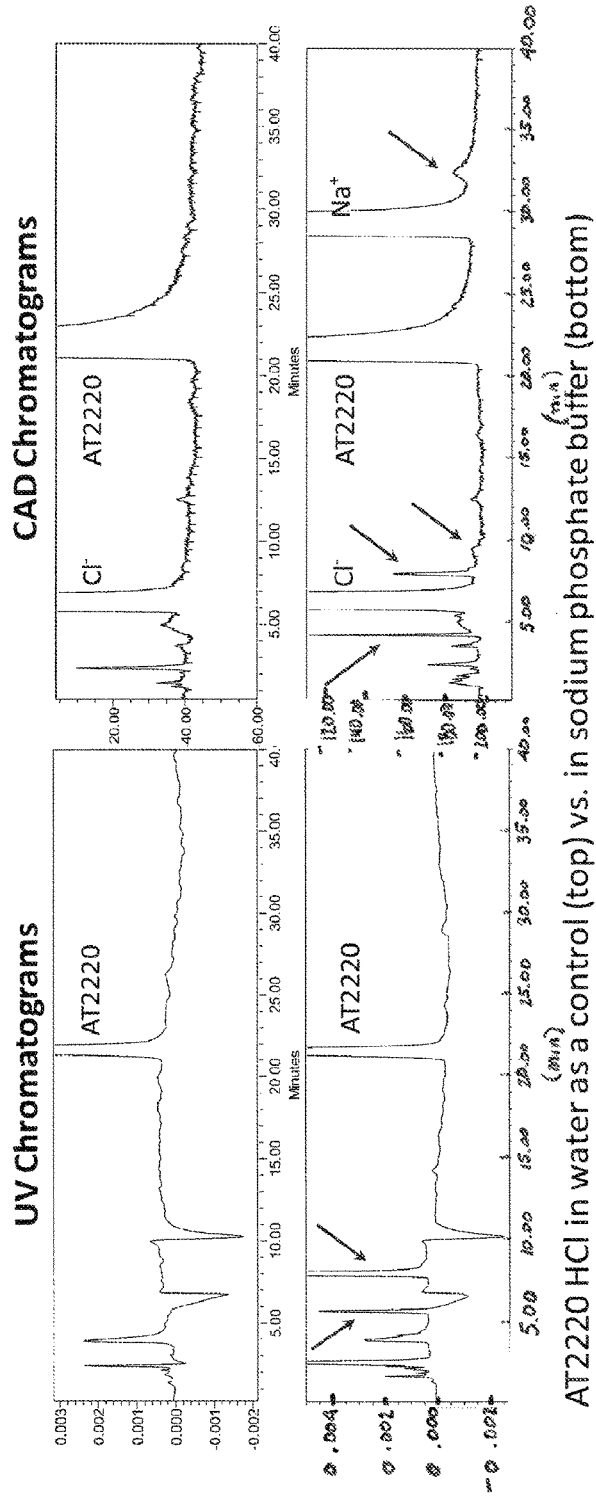
FIG. 1 shows stability of 1-deoxynojirimycin hydrochloride (1-DNJ-HCl or AT2220) in sodium phosphahate buffer solution compared to stability in water as described in Example 2. The stability was measured by normal phase high performance liquid chromatography (NP-HPLC). The left spectra shows 1-deoxynojirimycin as detected by UV detector, while the right spectra show 1-deoxynojirimycin as detected by Charged Aerosol Detector (CAD).

The presently disclosed parenteral formulations include 1-DNJ (also referred to as DNJ), or a salt or derivative thereof. In one embodiment, the parenteral formulation includes 1-DNJ-HCl. In another embodiment, the formulation includes a derivative of 1-DNJ, such as N-butyl deoxynojirimycin. The derivative of 1-DNJ (e.g., N-butyl deoxynojirimycin) may be found in addition to, or in place of, 1-DNJ or 1-DNJ-HCl.

As noted above, the active agent is selected from 1-deoxynojirimycin, a pharmaceutically acceptable salt thereof, or a derivative thereof. The concentration of the active agent in the formulation can, in certain non-limiting embodiments, range from about 10 mg/ml to about 100 mg/ml, or from about 20 mg/mgl to about 50 mg/ml, or from about 20 mg/ml to about 35 mg/ml. In some embodiments the concentration of the active agent in the formulation can be 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml or 35 mg/ml. In some embodiments the concentration of the active agent in the formulation can be about 30 mg/ml. In some embodiments concentration of 1-deoxynojirimycin as a free base in the formulation can be about 25 mg/ml In certain embodiments, the pH of the formulation is from about 3 to about 9 or to about 10, or from about 3 to about 6, or from about 3.0 to about 5.5. In one embodiment, the pH of the formulation is below 6.0, or below 5.5. It has been found that discoloration may occur in 1-DNJ/buffer formulations with a pH in the range of about 6.0-7.5. In some embodiments the pH of the formulation can be 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9 or 6.0. In some embodiments the pH of the formulation can be about 5.0.

The formulation can contain a buffer. In one embodiment, the buffer is selected from sodium citrate, sodium acetate and sodium phosphate. In one embodiment, the buffer is sodium citrate. Other salts known to be used with buffers, besides sodium salts, can also be used, such as potassium and ammonium salts. Thus, the buffer can be, for example, a potassium citrate, potassium acetate or potassium phosphate buffer, or an ammonium citrate, ammonium acetate or ammonium phosphate buffer. The concentration of the buffer can, in certain non-limiting embodiments, range from about 20 mM to about 75 mM, or from about 30 mM to about 60 mM, or from about 35 mM to about 55 mM. In some embodiments the concentration of the buffer can be 30 mM, 31 mM, 32 mM, 32 mM, 33 mM, 34 mM, 35 mM, 36 mM, 37 mM, 38 mM, 39 mM, 40 mM, 41 mM, 42 mM, 45 mM, 46 mM, 47 mM, 48 mM, 49 mM, 50 mM, 51 mM, 52 mM, 53 mM, 54 mM, 55 mM, 56 mM, 57 mM, 58 mM, 59 mM or 60 mM. In some embodiments the concentration of the buffer can be about 50 mM.

In some embodiments the formulation includes a chelating agent, such as EDTA or EGTA. In some embodiments, EDTA is present in the formulation at a concentration from 0.005% to 0.25% (w/v), or from 0.01% to 0.1% (w/v). In one embodiment, EDTA is present in the formulation at a concentration of about 0.05% (w/v).

In one embodiment, the presently disclosed parenteral formulation is stored under a nitrogen atmosphere. In one embodiment, the presently disclosed parenteral formulation is stored under an air atmosphere. In one embodiment, the presently disclosed parenteral formulation are stored under a combination of nitrogen and air atmosphere. In one embodiment, the presently disclosed parenteral formulation are stored at below 45° C., or below 25° C., or below 15° C., or below 10° C.

In one embodiment, the osmolality of the presently disclosed parenteral formulation ranges from about 280 to about 320 mOsm/kg. In an alternative embodiment, the osmolality of the presently disclosed is below about 500 mOsm/kg, or below about 450 mOsm/kg. In one embodiment, the concentration of 1-DNJ-HCl is about 30 mg/mL, the concentration of the buffer is 40 mM and osmolality of about 374 mOsm/kg. In another embodiment, the concentration of 1-DNJ as a free base is about 25 mg/mL, the concentration of the buffer is 40 mM and osmolality of about 374 mOsm/kg. In another embodiment, the concentration of 1-DNJ-HCl is about 30 mg/mL, the concentration of the buffer is 50 mM and osmolality of about 400 mOsm/kg. In another embodiment, the concentration of 1-DNJ as a free base is about 25 mg/mL, the concentration of the buffer is 50 mM and osmolality of about 400 mOsm/kg. In other embodiments 1-DNJ-HCl concentration will be from about 30 mg/mL to about 60 mg/mL.

In one embodiment the formulation is suitable for subcutaneous administration. In one embodiment the formulation is suitable for intravenous (IV) administration.

In one embodiment, the 1-DNJ-HCl is present at a concentration of about 30 mg/mL and the buffer is present at a concentration of about 50 mM at pH of about 5. In one embodiment, the 1-DNJ, as a free base is present at a concentration of about 25 mg/mL and the buffer is present at a concentration of about 50 mM at pH of about 5. In one embodiment, the formulation is stored under the nitrogen atmosphere and at a temperature of from about 2° C. to about 8° C. In one embodiment, the formulation is stored under the nitrogen atmosphere and at a temperature of from about 23° C. to about 27° C. In one embodiment, the formulation is stored under the nitrogen atmosphere and at a temperature of from about 38° C. to about 42° C.

In one embodiment, the pharmaceutical composition contains 30 mg/mL of 1-DNJ-HCL at pH 5 and a 40 mM sodium citrate buffer. In one embodiment, the pharmaceutical composition contains 25 mg/mL of 1-DNJ, as a free base at pH 5 and a 40 mM sodium citrate buffer. In one embodiment, the pharmaceutical composition contains 30 mg/mL of 1-DNJ-HCL at pH 5, 40 nM sodium citrate buffer and 0.05% w/v EDTA. In one embodiment, the pharmaceutical composition contains 25 mg/mL of 1-DNJ, as a free base at pH 5, 40 nM sodium citrate buffer and 0.05% w/v EDTA. In one embodiment, the pharmaceutical composition contains 30 mg/mL of 1-DNJ-HCL at pH 5 and a 40 mM sodium acetate buffer. In one embodiment, the pharmaceutical composition contains 25 mg/mL of 1-DNJ, as a free base, at pH 5 and a 40 mM sodium acetate buffer. In one embodiment, the pharmaceutical composition contains 30 mg/mL of 1-DNJ-HCL at pH 5, 40 mM sodium acetate buffer and 0.05% w/v EDTA. In one embodiment, the pharmaceutical composition contains 25 mg/mL of 1-DNJ, as a free base, at pH 5, 40 mM sodium acetate buffer and 0.05% w/v EDTA.

In one embodiment, the pharmaceutical composition contains 30 mg/mL of 1-DNJ-HCL at pH 5 and a 50 mM sodium citrate buffer. In one embodiment, the pharmaceutical composition contains 30 mg/mL of 1-DNJ-HCL at pH 5, 50 nM sodium citrate buffer and 0.05% w/v EDTA. In one embodiment, the pharmaceutical composition contains 30 mg/mL of 1-DNJ-HCL at pH 5 and a 50 mM sodium acetate buffer. In one embodiment, the pharmaceutical composition contains 30 mg/mL of 1-DNJ-HCL at pH 5, 50 mM sodium acetate buffer and 0.05% w/v EDTA.

In one embodiment, the pharmaceutical composition contains 25 mg/mL of 1-DNJ, as a free base, at pH 5 and a 50 mM sodium citrate buffer. In one embodiment, the pharmaceutical composition contains 25 mg/mL of 1-DNJ, as a free base, at pH 5, 50 nM sodium citrate buffer and 0.05% w/v EDTA. In one embodiment, the pharmaceutical composition contains 25 mg/mL of 1-DNJ, as a free base, at pH 5 and a 50 mM sodium acetate buffer. In one embodiment, the pharmaceutical composition contains 25 mg/mL of 1-DNJ, as a free base, at pH 5, 50 mM sodium acetate buffer and 0.05% w/v EDTA.

Other pharmaceutically acceptable excipients which may be included in the formulation as buffers include bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrollidone; sugars, such as dextran, mannitol, sorbitol, and glycerol; propylene glycol and polyethylene glycol (e.g., PEG-4000, PEG-6000); glycerol; glycine or other amino acids; and lipids. A non-exclusive list of acceptable excipients is listed in the Table 1.

TABLE 1

List of excipients

| Excipient | pH Range |
|---|---|
| Acetate | |
| Sodium | 2.5-7.0 |
| Acetic acid | 2.5-7.2 |
| Glacial acetic acid | 3.5-7.0 |
| Ammonium | 6.8-7.8 |
| Ammonium sulfate | — |
| Ammonium hydroxide | — |
| Arginine | 7.0-7.4 |
| Aspartic acid | 5.0-5.6 |
| Benzene sulfonic acid | 3.25-3.65 |
| Benzoate sodium/acid | 3.5-6.9 |
| Bicarbonate, sodium | 5.5-11.0 |
| Boric acid/sodium | — |
| Carbonate, sodium | 4.0-11.0 |

TABLE 1-continued

List of excipients

| Excipient | pH Range |
|---|---|
| Citrate | |
| Acid | 2.5-9.0 |
| Sodium | 3.0-8.5 |
| Disodium | 6.1 |
| Trisodium | 6.1 |
| Diethanolamine | 9.5-10.5 |
| Glucono delta lactone | 5.5-7.0 |
| Glycine/glycine HCl | 2.5-10.8 |
| Histidine/histidine HCl | 5.0-6.5 |
| Hydrochloric acid | Broad range |
| Hydrobromic acid | 3.5-6.5 |
| Lactate sodium/acid | 2.7-5.8 |
| Lysine (L) | — |
| Maleic acid | 3.0-5.0 |
| Megulmine | 6.5-11.0 |
| Methanesulfonic acid | 3.2-4.0 |
| Monoethanolamine | 8.0-9.0 |
| Phosphate | |
| Acid | 6.5-8.5 |
| Monobasic potassium | 6.7-7.3 |
| Dibasic potassium | 6.7-7.3 |
| Monobasic sodium | 2.5-8.0 |
| Dibasic sodium | 2.5-8.3 |
| Tribasic sodium | — |
| Sodium hydroxide | Broad range |
| Succinate sodium/disodium | 5.0-6.0 |
| Sulfuric acid | 3.0-7.0 |
| Tartrate sodium/acid | 2.5-6.2 |
| Tromethamine (Tris) | 6.5-9.0 |

Adapted from: Nema, S et. al. (2011). Excipients and their role in approved injectable products: current usage and future directions. PDA J Pharm Sci and Tech, 65, 287-332.

EXAMPLES

Example 1.

Preparation of Buffers

The following representative buffer compositions were prepared by admixing the ingredients set forth below. The buffers used in Examples 2-6 below were prepared in a similar fashion, amounts of acidic and basic components modified, if necessary, to obtain the pH parameters specified therein.

TABLE 2

Components of 50 mM sodium citrate buffer, pH 5

| Component | Amount per ml |
|---|---|
| Sodium Citrate Dihydrate | 9.32 mg |
| Citric Acid Monohydrate | 3.85 mg |
| Water | q.s. to 1.0 mL |

TABLE 3

Components of 50 mM sodium acetate buffer, pH 5.5

| Component | Amount per ml |
|---|---|
| Sodium Acetate Trihydrate | 5.92 mg |
| Glacial Acetic Acid | 0.384 mg |
| Water | q.s. to 1.0 mL |

TABLE 4

Components of 100 mM sodium phosphate buffer, pH 7

| Component | Amount per ml |
|---|---|
| Sodium Phosphate Monobasic Monohydrate | 4.79 mg |
| Sodium Phosphate Dibasic, Anhydrous | 9.26 mg |
| Water | q.s. to 1.0 mL |

Deionized and/or distilled water can be used in place of water.

Example 2.

Stability and Integrity of 1-Deoxynojirimycin Chloride in 100 mM Sodium Phosphate Buffer Solution 1-DNJ-HCl was dissolved in sodium phosphate buffer. 1-DNJ-HCl concentration was 60 mg/mL; sodium phosphate buffer concentration was 100 mM at pH 4.89. The formulation was stored at 60° C. for 4 days. 1-DNJ-HCl solution in water was used as a control. Reaction rate for small molecules such as 1-DNJ-HCl generally follows Arrhenius equation where reaction rate nearly doubles for every 10° C. increase in the temperature. Thus, under this model, the reaction rate at 60° C. would be $2^5$ or 32 times the reaction rate at 10° C. Therefore during 4 days at 60° C. 1-DNJ-HCl would degrade by approximately the same percentage as during 128 days (4*32) at 10° C.

The stability of 1-DNJ-HCl was measured by normal phase high performance liquid chromatography (NP-HPLC). 1-DNJ-HCl was recorded by UV chromatograms and by Charged Aerosol Detector (CAD) chromatograms. Mobile phase consisted of ACN/30 mM Ammonium Acetate (90/10, v/v). The flow rate was 1.0 ml/min with 5 µl injection at 400° C. UV absorbance was measured at 220 nm. CAD detector settings were 35.0 psi, Gain: 100 pA.

Results:

The results are shown in the FIG. 1. 1-DNJ-HCl was still present in the sodium phosphate buffer solution after 4 days at 60° C. Additionally, both UV and CAD chromatograms detected presence of new compounds in the phosphate buffer solution. The peaks, corresponding to the new compounds are highlighted by the red arrows on the FIG. 1. Additionally a discoloration of the phosphate buffer solution was observed. No new compounds were detected in the control 1-DNJ-HCl aqueous solution. The aqueous solution remainded clear after 4 days at 60° C.

Inclusion of 1-DNJ-HCl in a sodium phosphate buffer in this Example resulted in discoloration of 1-DNJ-HCl. Furthermore, High Performance Liquid Chromatography (HPLC) indicated presence of additional compounds in 1-DNJ-HCl formulation in the sodium phosphate buffer. The presence of additional compounds indicated that 1-DNJ-HCl is not stable in the sodium phosphate buffer under the conditions of this Example.

Example 3.

Stability and Integrity of 1-Deoxynojirimycin Chloride in 50 mM Sodium Acetate Buffer Solution 1-DNJ-HCl was dissolved in sodium acetate buffer. The 1-DNJ-HCl concentration was 60 mg/mL; sodium acetate buffer concentration was 50 mM at pH 5.5. The formulation was stored at 60° C. for 4 days. 1-DNJ-HCl solution in water was used as control. Reaction rate for small molecules such as 1-DNJ-HCl generally follows the Arrhenius equation, in which the reaction rate nearly doubles for every 10° K increase in the temperature. Thus the reaction rate, under this model, at 60° C. would be $2^5$ or 32 times the reaction rate at 10° C. Therefore during 4 days at 60° C. 1-DNJ-HCl would degrade by approximately same percentage as during 128 clays at at 10° C.

Figure 2:
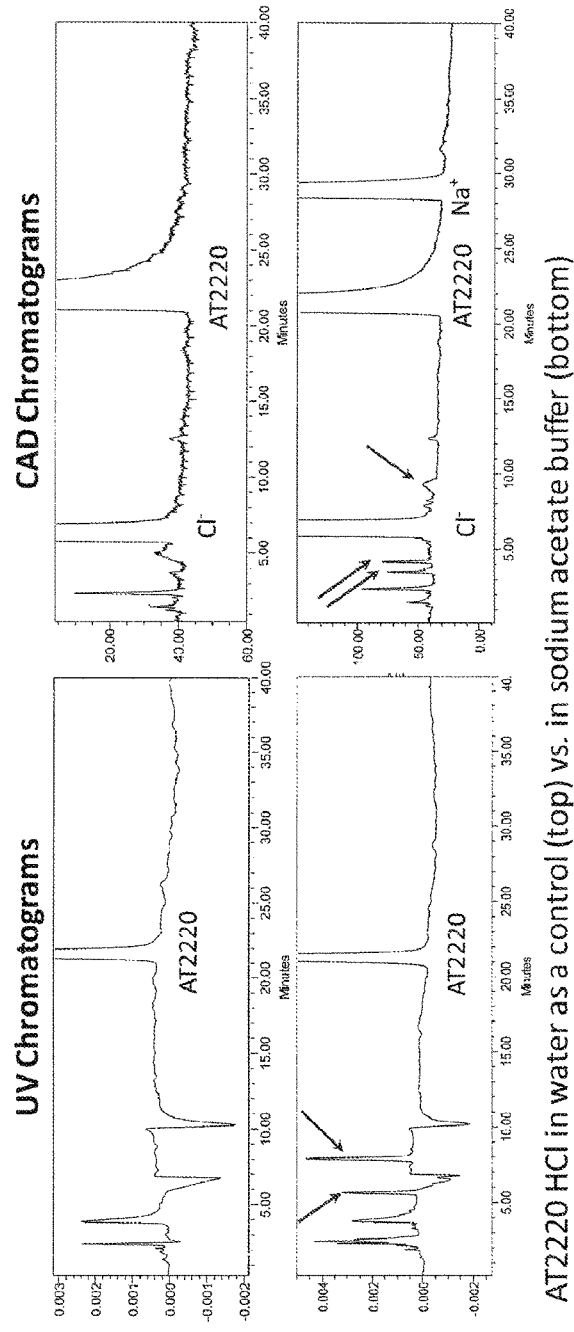
FIG. 2 shows stability of 1-deoxynojirimycin chloride in sodium acetate buffer solution compared to stability in water as described in Example 3. The stability was measured by normal phase high performance liquid chromatography (NP-HPLC). The left spectra shows 1-deoxynojirimycin as detected by UV detector, while the right spectra show 1-deoxynojirimycin as detected by Charged Aerosol Detector (CAD).

The stability of 1-DNJ-HCl was measured by NP-HPLC. Presence of 1-DNJ-HCl was recorded by UV absorbance detector and by Charged Aerosol Detector. Mobile phase consisted of ACN/30 mM Ammonium Acetate (90/10, v/v). The flow rate was 1.0 ml/min with 5 µl injection at 400 C. UV absorbance was measured at 220 nm. CAD detector settings were 35.0 psi, Gain: 100 pA.
Results:

The results are shown in the FIG. 2. 1-DNJ-HCl was still present in the sodium acetate buffer solution after 4 days at 60° C. Additionally, both UV and CAD chromatograms detected presence of new compounds in the acetate buffer solution. The peaks, corresponding to the new compounds are highlighted by the red arrows in FIG. 2. Additionally a discoloration of the acetate buffer solution was observed. No new compounds were detected in the control 1-DNJ-HCl aqueous solution. The aqueous solution remainded clear after 4 days at 60° C.

Example 4.

Stability and Integrity of 1-Deoxynojirimycin Chloride in 50 mM Sodium Citrate Buffer Solution with EDTA Under Nitrogen Atmosphere 1-DNJ-HCl was dissolved in sodium citrate buffer that further includes EDTA. 1-DNJ-HCl concentration was 60 mg/mL; sodium citrate buffer concentration was 50 mM at pH 4.6. The EDTA concentration was 0.05% w/v. Some samples were stored under the nitrogen atmosphere (essentially 100% nitrogen) while others were stored under air. The formulation was stored at 60° C. for 8 days.

Figure 3:
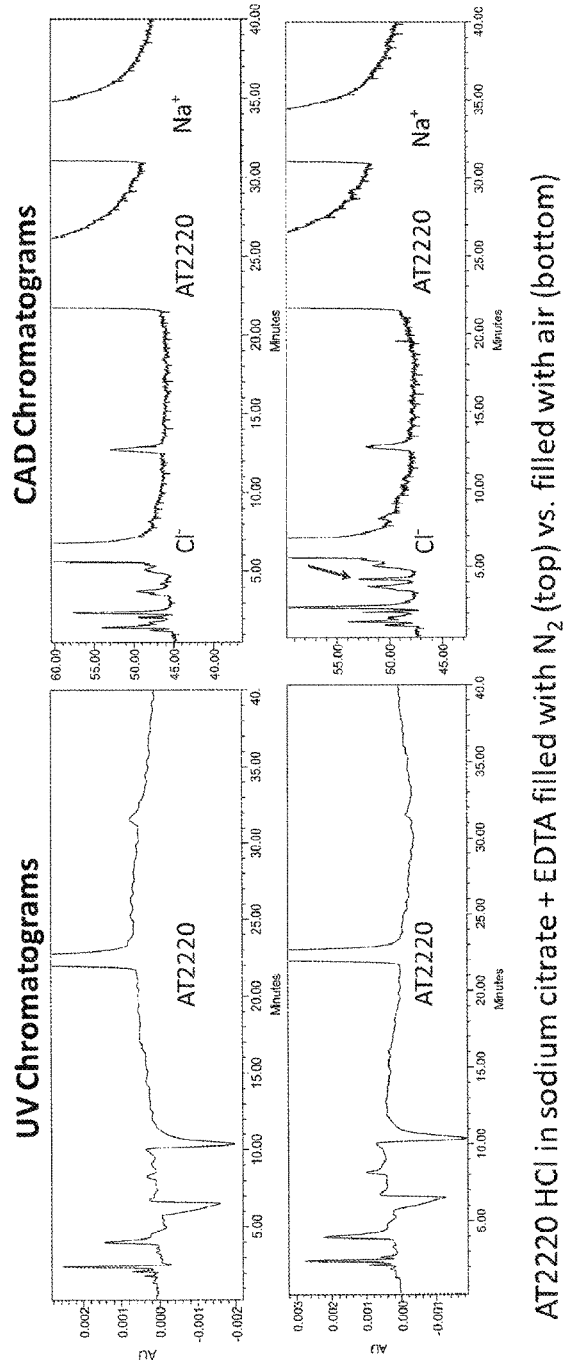
FIG. 3 shows stability of 1-deoxynojirimycin chloride in sodium citrate buffer solution with an addition of EDTA under the nitrogen atmosphere as described in Example 4. The stability was measured by normal phase high performance liquid chromatography (NP-HPLC). The left spectra shows 1-deoxynojirimycin as detected by UV detector, while the right spectra show 1-deoxynojirimycin as detected by Charged Aerosol Detector (CAD).

Stability of 1-DNJ-HCl was measured by NP-HPLC. Presence of 1-DNJ-HCl was recorded by UV absorbance detector and by Charged Aerosol Detector. Mobile phase consisted of ACN/30 mM Ammonium Acetate (90/10, v/v). The flow rate was 1.0 ml/min with 5 µl injection at 400 C. UV absorbance was measured at 220 nm. CAD detector settings were 35.0 psi, Gain: 100 pA.
Results:

The results are shown in the FIG. 3. 1-DNJ-HCl was still present in the sodium citrate buffer solution after 8 days at 60° C. No new compounds were detected in the samples stored under nitrogen atmosphere. The solution remained clear with no visible discoloration. A combination of nitrogen atmosphere and EDTA preserved stability and integrity of AT2220. The samples stored under air showed presence of new compounds in the acetate buffer solution. The amount of these compounds was lower than in Examples 1 and 2, based on number and size of the additional peaks. The peaks corresponding to the new compounds are highlighted by the red arrows in FIG. 3. Additionally slight discoloration of the citrate buffer formulation, stored under air was observed.

Example 5.

Stability and Integrity of 1-Deoxynojirimycin Chloride in 50 mM Sodium Citrate Buffer Solution 1-DNJ-HCl was dissolved in sodium citrate buffer. 1-DNJ-HCl concentration was 60 mg/mL; sodium citrate buffer concentration was 50 mM at pH 4.7. The formulation was stored at 60° C. for 8 days. 1-DNJ-HCl solution in water was used as control.

Figure 4:
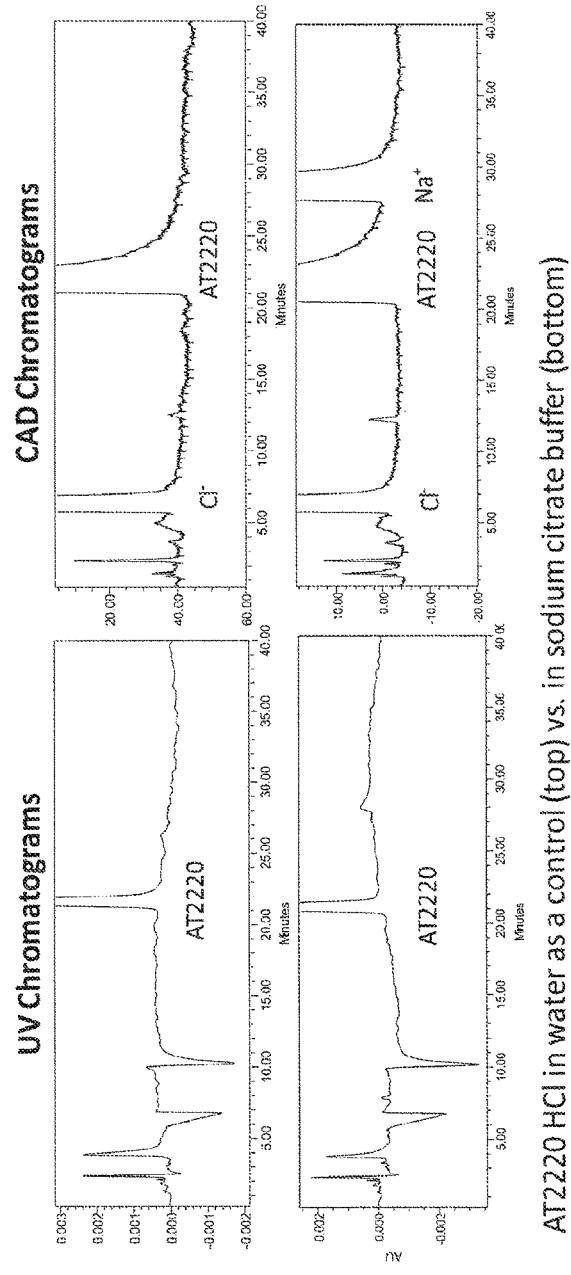
FIG. 4 shows stability of 1-deoxynojirimycin chloride in sodium citrate buffer solution compared to stability in water as described in Example 5. The stability was measured by normal phase high performance liquid chromatography (NP-HPLC). The left spectra shows 1-deoxynojirimycin as detected by UV detector, while the right spectra show 1-deoxynojirimycin as detected by Charged Aerosol Detector (CAD).

Stability of 1-DNJ-HCl was measured by NP-HPLC. Presence of 1-DNJ-HCl was recorded by UV absorbance detector and by Charged Aerosol Detector. Mobile phase consisted of ACN/30 mM Ammonium Acetate (90/10, v/v). The flow rate was 1.0 ml/min with 5 µl injection at 400 C. UV absorbance was measured at 220 nm. CAD detector settings were 35.0 psi, Gain: 100 pA.
Results:

The results are shown in the FIG. 4. 1-DNJ-HCl was still present in the sodium citrate buffer solution after 8 days at 60° C. Based on these results, EDTA does not appear required for 1-DNJ-HCl formulation stability. No new compounds were detected in the control 1-DNJ-HCl aqueous solution. No discoloration was observed in the aqueous solution after 8 days at 60° C.

Example 6.

Stability and Integrity of 1-Deoxynojirimycin Chloride in 50 mM Sodium Citrate Buffer Solution Under Nitrogen Atmosphere 1-DNJ-HCl was dissolved in sodium citrate buffer. 1-DNJ-HCl concentration was 60 mg/mL; sodium citrate buffer concentration was 50 mM at pH 5.0. The formulation was stored at 60° C. for 17 days. The samples were stored under the nitrogen atmosphere (essentially 100% nitrogen). 1-DNJ-HCl solution in water was used as control. Reaction rate for small molecules such as 1-DNJ-HCl generally follows Arrhenius equation where reaction rate nearly doubles for every 10° K increase in the temperature. Thus reaction rate at 60° C. would be $2^5$ or 32 times the reaction rate at 10° C. Therefore during 17 days at 60° C. AT2220 would degrade, under this model, by approximately same percentage as during 17 multiplied by 32 days or about 17 months.

Stability of 1-DNJ-HCl was measured by NP-HPLC. Presence of 1-DNJ-HCl was recorded by UV absorbance detector and by Charged Aerosol Detector. Mobile phase consisted of ACN/30 mM Ammonium Acetate (90/10, v/v). The flow rate was 1.0 ml/min with 5 µl injection at 400° C. UV absorbance was measured at 220 nm. CAD detector settings were 35.0 psi, Gain: 100 pA.
Results:

The results are shown in FIG. 4. 1-DNJ-HCl was still present in the sodium citrate buffer solution after 17 days at 60° C. under nitrogen atmosphere. No new compounds were detected in the control 1-DNJ-HCl aqueous solution. No discoloration was observed in the aqueous solution after 17 days at 60° C.

In summary, 1-DNJ-HCl formulations in sodium phosphate and sodium acetate buffers resulted in discoloration. Furthermore, HPLC indicated presence of additional compounds in 1-DNJ-HCl formulation in the sodium phosphate and sodium acetate buffer. In contrast, 1-DNJ-HCl formulation in sodium citrate buffer showed little to no discoloration and little to no presence of additional compounds. Based on the results of these Examples, 1-DNJ-HCl formulation is most stable in sodium citrate buffer.

Storage of samples under nitrogen atmosphere (essentially 100%) nitrogen preserves stability and integrity of 1-deoxynojirimycin chloride formulation greater than storage under air. (See examples 3 and 5).

Based on the results of these Examples, the presence of EDTA is not necessary for preserving stability and integrity of 1-deoxynojirimycin chloride formulations. (See examples 4 and 5).

Example 7.

Measurement of 1-Deoxynojirimycin Chloride Osmolality in Sodium Citrate Buffer

The molallity of 1-deoxynojirimycin chloride (1-DNJ-HCl) was determined by freezing point depreciation. 1-deoxynojirimycin chloride concentration ranged from 30 mg/mL to 60 mg/mL. Sodium citrate concentration ranged from 20 to 50 mM.
Results:
The results are presented below in Table 5.

TABLE 5

1-deoxynojirimycin chloride osmolality

| 1-DNJ-HCl (mg/mL) | Osmolality (mOsm/kg) Sodium Citrate Buffer Concentration | | | | | | |
|---|---|---|---|---|---|---|---|
| | 50 mM | 45 mM | 40 mM | 35 mM | 30 mM | 25 mM | 20 mM |
| 60 | 654 | 638 | 623 | 607 | 592 | 576 | 560 |
| 55 | 613 | 597 | 581 | 566 | 550 | 535 | 519 |
| 50 | 571 | 555 | 540 | 524 | 509 | 493 | 477 |
| 45 | 530 | 514 | 498 | 483 | 467 | 452 | 436 |
| 40 | 488 | 472 | 457 | 441 | 426 | 410 | 394 |
| 35 | 447 | 431 | 415 | 400 | 384 | 369 | 353 |
| 30 | 405 | 389 | 374 | 358 | 343 | 327 | 311 |

The results show that 1-DNJ-HCl concentration of 30 mg/mL (resulting in free 1-DNJ concentration of 25 mg/mL) in 50 mM Sodium Citrate buffer will result in osmolality of 405 mOsm/kg. Ideally osmolality of the formulation for parenteral formulation would be 280-320 mOsm/kg so that the formulation would be isotonic with the target tissue or blood. Osmolality of about 500 mOsm/kg or below is generally regarded as acceptable for clinical trials as it does not cause deleterious health effects when administered to a human, such as irritation.

Example 8.

Stability of 1-DNJ-HCl Formulation at Different Temperatures (Appearance and Color)

1-DNJ-HCl was dissolved in sodium citrate buffer. 1-DNJ-HCl concentration was 30 mg/mL (resulting free 1-DNJ concentration was 25 mg/mL); sodium citrate buffer concentration was 50 mM at pH 5.0. Two batches were made each containing about a thousand samples. L-12-026 batch was stored for 6 months and E-13-014 batch was stored for 3 months. The samples were stored under the nitrogen atmosphere (essentially 100% nitrogen). 1-DNJ-HCl solution in water was used as control. The samples were stored at three different temperatures: 5° C.±3° C., 25° C.±2° C. or 40° C.±2° C. At 1, 3 and 6 months samples from each batch were collected and product stability was measured. Appearance and color was measured in APHA units. Appearance of below 100 APHA units is generally regarded as acceptable for clinical trials as an indication of stability.
Results:
Results are presented below in Tables 6.1-6.3. All samples appear as clear colorless solutions.

TABLE 6.1

Drug Product Stability Data for Appearance and Color at 5° C. ± 3° C. Storage Conditions.

| Batch | Time (Months) | | | |
|---|---|---|---|---|
| | 0 | 1 | 3 | 6 |
| L-12-026 | Conforms 0 | Conforms 0 | Conforms 0 | Conforms 0 |
| E-13-014 | Conforms 0 | Conforms 0 | Conforms 0 | — |

TABLE 6.2

Drug Product Stability Data for Appearance and Color at 25° C. ± 2° C. Storage Conditions.

| Batch | Time (Months) | | | |
|---|---|---|---|---|
| | 0 | 1 | 3 | 6 |
| L-12-026 | Conforms 0 | Conforms 0 | Conforms <10 | Conforms 0 |
| E-13-014 | Conforms 0 | Conforms 0 | Conforms 0 | — |

TABLE 6.3

Drug Product Stability Data for Appearance and Color at 40° C. ± 2° C. Storage Conditions.

| Batch | Time (Months) | | | |
|---|---|---|---|---|
| | 0 | 1 | 3 | 6 |
| L-12-026 | Conforms 0 | Conforms 0 | Conforms <10 | Conforms 10 |
| E-13-014 | Conforms 0 | Conforms 0 | Conforms 0 | — |

Results show that 1-DNJ-HCl formulation remains surprisingly stable. No discoloration is observed during 6 months storage at temperatures ranging from about 2° C. to about 42° C.

Example 9.

Stability of 1-DNJ-HCl Formulation at Different Temperatures (Osmolality)

1-DNJ-HCl was dissolved in sodium citrate buffer, under conditions described in Example 8. The samples were stored at two different temperatures: 5° C.±3° C. or 25° C.±2° C. At 1, 3 and 6 months samples from each batch were collected and osmomolality was measured. Initial Osmomolality of the sample was about 405 mOsm/kg. Osmolality of about 300-500 mOsm/kg is generally regarded as acceptable for clinical trials.

Results:

Results are presented below in Tables 7.1-7.2.

TABLE 7.1

Drug Product Stability Data for Osmolality at 5° C. ± 3° C. Storage Conditions.

| Batch | Time (Months) | | | |
|---|---|---|---|---|
| | 0 | 1 | 3 | 6 |
| L-12-026 | 403 | 403 | 403 | 404 |
| E-13-014 | 403 | 405 | 405 | — |

TABLE 7.2

Drug Product Stability Data for Osmolality at 25° C. ± 2° C. Storage Conditions.

| Batch | Time (Months) | | | |
|---|---|---|---|---|
| | 0 | 1 | 3 | 6 |
| E-13-014 | 403 | 407 | 407 | — |

Results show that the formulation demonstrates a remarkable stability. Osmolality remains unchanged after storage for 3 and 6 months at temperatures ranging from about 2° C. to about 27° C. Furthermore, no trend to decrease osmolality is observed. Without being bound by a particular theory, the data indicates that osmolality is not going to significantly change during storage periods of about a year or longer.

Example 10.

Stability of 1-DNJ-HCl Formulation at Different Temperatures (Particulate Matter)

1-DNJ-HCl was dissolved in sodium citrate buffer, under conditions described in Example 8. The samples were stored at two different temperatures: 5° C.±3° C. or 25° C.±2° C. At 1, 3 and 6 months samples from each batch were collected and presense of particulate matter was measured as number of particles per container. Particles of two sizes were considered separately: particles greater or equal to 10 μm and particles greater or equal to 25 μm. Presense of particicules greater or equal to 10 μm in the amount of less or equal to about 6000 per 10 mL container is generally regarded as acceptable for clinical trials. Presense of particules greater or equal to 25 μm in the amount of less or equal to about 600 per 10 mL container is generally regarded as acceptable for clinical trials.

Results:

Results are presented below in Tables 8.1-8.2. Number of particles in each sample is shown,

TABLE 8.1

Drug Product Stability Data for Particulate Matter at 5° C. ± 3° C. Storage Conditions.

| Batch | Time (Months) | | | |
|---|---|---|---|---|
| | 0 | 1 | 3 | 6 |
| L-12-026 ≥10 μm: | 5 | 7 | 12 | 181 |
| L-12-026 ≥25 μm: | <1 | 3 | 0 | 9 |
| E-13-014 ≥10 μm: | 181 | 5 | 7 | — |
| E-13-014 ≥25 μm: | 9 | 1 | 1 | |

TABLE 8.2

Drug Product Stability Data for Particulate Matter at 25° C. ± 2° C. Storage Conditions.

| Batch | Time (Months) | | | |
|---|---|---|---|---|
| | 0 | 1 | 3 | 6 |
| E-13-014 ≥10 μm: | 181 | 1 | 3 | — |
| E-13-014 ≥25 μm: | 9 | 0 | 1 | — |

Results show that the formulation demonstrates a remarkable stability. There is no increase of particular matter of any kind after storage for 3 and 6 months at temperatures ranging from about 2° C. to about 27° C. Furthermore, increase in particulate matter greater or equal to 25 μm. It indicates that particles do not aggregate to form larger particles. Without being bound by a particular theory the data indicates that amount of particles is not going to increase during storage periods of about a year or longer.

Example 11.

Stability of 1-DNJ-HCl Formulation at Different Temperatures (pH)

1-DNJ-HCl was dissolved in sodium citrate buffer, under conditions described in Example 8. The samples were stored at three different temperatures: 5° C.±3° C., 25° C.±2° C. or 40° C.±2° C. At 1, 3 and 6 months samples from each batch were collected and pH was measured. Initial pH of the solution was 5.0. Maintaining pH in the range of about 4.8 to about 5.4 is considered as acceptable indication of stability.

Results:

Results are presented below in Tables 9.1-9.3.

TABLE 9.1

Drug Product Stability Data for pH at 5° C. ± 3° C. Storage Conditions.

| Batch | Time (Months) | | | |
|---|---|---|---|---|
| | 0 | 1 | 3 | 6 |
| L-12-026 | 5.1 | 5.0 | 5.0 | 5.0 |
| E-13-014 | 4.9 | 4.9 | 5.0 | — |

TABLE 9.2

Drug Product Stability Data for pH at 25° C. ± 2° C. Storage Conditions.

| Batch | Time (Months) | | | |
|---|---|---|---|---|
| | 0 | 1 | 3 | 6 |
| L-12-026 | 5.1 | 5.0 | 5.0 | 5.0 |
| E-13-014 | 4.9 | 5.0 | 5.0 | — |

TABLE 9.3

Drug Product Stability Data for Appearance and Color at 40° C. ± 2° C. Storage Conditions.

| Batch | Time (Months) | | | |
|---|---|---|---|---|
| | 0 | 1 | 3 | 6 |
| L-12-026 | 5.1 | 5.0 | 5.0 | 5.0 |
| E-13-014 | 4.9 | 4.9 | 5.0 | — |

Results show that the formulation demonstrates remarkable stability. There is no change of any kind in pH after storage for 3 and 6 months at temperatures ranging from about 2° C. to about 42° C. Without being bound by a particular theory the data indicates that pH of the formulation is not going to increase during storage periods of about a year or longer.

Example 12.

Stability of 1-DNJ-HCl Formulation at Different Temperatures (Concentration)

1-DNJ-HCl was dissolved in sodium citrate buffer, under conditions described in Example 8. The samples were stored at three different temperatures: 5° C.±3° C., 25° C.±2° C. or 40° C.±2° C., At 1, 3 and 6 months samples from each batch were collected and concentration of 1-DNJ as a free base was measured. Initial concentration of 1-DNJ as a free base in the solution was about 25 mg/mL (corresponding to 30 mg/mL of 1-DNJ HCl). Maintaining concentration of 1-DNJ as a free base in the range of about 22 to about 27 mg/mL (90-110%) is considered as acceptable indication of stability. Results:

Results are presented below in Tables 10.1-10.3.

TABLE 10.1

Drug Product Stability Data for pH at 5° C. ± 3° C. Storage Conditions.

| Batch | Time (Months) | | | |
|---|---|---|---|---|
| | 0 | 1 | 3 | 6 |
| L-12-026 | 26.9 (110%) | 25.5 (104%) | 25.6 (104%) | 26.0 (106%) |
| E-13-014 | 25.7 (103%) | 26.1 (104%) | 27.0 (108%) | — |

TABLE 10.2

Drug Product Stability Data for pH at 25° C. ± 2° C. Storage Conditions.

| Batch | Time (Months) | | | |
|---|---|---|---|---|
| | 0 | 1 | 3 | 6 |
| L-12-026 | 26.9 (110%) | 25.7 (105%) | 25.6 (104%) | 25.9 (106%) |
| E-13-014 | 25.7 (103%) | 25.2 (101%) | 25.7 (103%) | — |

TABLE 10.3

Drug Product Stability Data for Appearance and Color at 40° C. ± 2° C. Storage Conditions.

| Batch | Time (Months) | | | |
|---|---|---|---|---|
| | 0 | 1 | 3 | 6 |
| L-12-026 | 26.9 (110%) | 25.5 (104%) | 24.4 (99%) | 26.2 (107%) |
| E-13-014 | 25.7 (103%) | 25.6 (102%) | 25.1 (100%) | — |

Results show that the formulation demonstrates a remarkable stability. There is no significant change of in concentration after storage for 3 and 6 months at temperatures ranging from about 2° C. to about 42° C. High concentration value at initial time point was caused by variability of reference standard injections and was not determined to be formulation or stability related. There is no visible pattern for increase or decrease in concentration. Without being bound by a particular theory the data indicates that concentration of the formulation is not going to increase during storage periods of about a year or longer.

Example 13.

Hemolytic Potential of 1-DNJ-HCl Formulation in Human, Rat, and Cynomolgus Monkey Whole Blood 1-DNJ-HCl was dissolved in sodium citrate buffer. 1-DNJ-HCl concentration was 30 mg/mL (resulting free 1-DNJ concentration was 25 mg/mL); sodium citrate buffer concentration was 50 mM at pH 5.0. 1-DNJ-HCl formulation was added to whole blood samples of male human, rat, and cynomolgus monkey. 500 μM of 1-DNJ-HCl formulation was mixed with 500 μM of blood sample. Buffer served as a negative control, while Triton-X 100 (Lysing agent) served as a positive control. Additionally blood sample without any additions was used as a negative control.

The samples were stored at 4° C. Blood samples were incubated at 37° C. for 30 minutes with the 1-DNJ-HCl formulation, after which the samples were centrifuged. The amount of hemoglobin in the supernatant from each centrifuged sample was measured using a commercially available hemoglobin assay kit (BioAssay Systems, QuantiChrom™ Hemoglobin Assay Kit) and the Tecan microplate reader. Results:

Results are presented below in Table 11.

TABLE 11

Hemolytic Potential of 1-DNJ-HCl in Whole Blood

| Species | Samples: 500 μL blood volume was mixed with 500 μL of the following: | Dilution | Avg OD (n = 4) | Std Dev (mg/dL) | Hemoglobin (mg/dL) | % RBC lysis |
|---|---|---|---|---|---|---|
| Human | 30 mg/mL AT2220 | 1 | 0.0755 | 0.005 | 19 | 0.0% |
| | Vehicle | 1 | 0.0706 | 0.005 | 18 | 0.0% |
| | — | 1 | 0.2568 | 0.030 | 64 | 0.7% |
| | 0.1% Triton X-100 | 100 | 0.2768 | 0.002 | 6899 | 100.0% |
| Monkey | 30 mg/mL AT2220 | 1 | 0.0649 | 0.004 | 16 | 0.1% |
| | Vehicle | 1 | 0.0488 | 0.001 | 12 | 0.0% |
| | — | 1 | 0.2989 | 0.036 | 74 | 1.3% |
| | 0.1% Triton X-100 | 100 | 0.2000 | 0.004 | 4984 | 100.0% |
| Rat | 30 mg/mL AT2220 | 1 | 0.3535 | 0.078 | 88 | −0.3% |
| | Vehicle | 1 | 0.4304 | 0.041 | 107 | 0.0% |
| | — | 1 | 0.5634 | 0.021 | 140 | 0.5% |
| | 0.1% Triton X-100 | 100 | 0.2567 | 0.007 | 6398 | 100.0% |

Results show that the formulation demonstrates a surprising lack of hemolytic potential. No hemolysis of erythrocytes in human, Sprague Dawley rat, or Cynomolgus monkey whole blood was detected with the vehicle or undiluted 1-DNJ-HCl formulation mixtures. The 1-DNJ-HCl formulation and its vehicle did not result in any detectable hemolysis in whole blood from any of the three species tested in this assay. Without being bound by a particular theory the data indicates that the formulation is not going to cause deleterious health effects such as pain or irritation when administered to the subject. The 1-DNJ-HCl formulation demonstrates a remarkable safety as it does not cause vascular irritation.

\*\*\*

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any linking agent, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

The invention claimed is:

1. A pharmaceutical composition comprising:
    a) an active agent selected from 1-deoxynojirimycin, a pharmaceutically acceptable salt thereof, or a derivative thereof, and
    b) a buffer,
wherein the active agent is present at a concentration of from about 1 mg/mL to about 100 mg/mL.

2. The pharmaceutical composition of claim 1, wherein the active agent comprises 1-deoxynojirimycin.

3. The pharmaceutical composition of claim 1 wherein the active agent comprises 1-deoxynojirimycin hydrochloride.

4. The pharmaceutical composition of claim 1, wherein the active agent comprises N-butyl-deoxynojirimycin, or a pharmaceutically acceptable salt thereof.

5. The pharmaceutical composition of claim 1, wherein the pharmaceutical composition is formulated for intravenous administration.

6. The pharmaceutical composition of claim 1, wherein the pharmaceutical composition is at a pH of from about 4 to about 6.

7. The pharmaceutical composition of claim 1, wherein the active agent is present at a concentration of from about 1 mg/mL to about 60 mg/mL.

8. The pharmaceutical composition of claim 1, wherein the active agent is present at a concentration of from about 25 mg/mL to about 30 mg/mL.

9. The pharmaceutical composition of claim 1, wherein the buffer is present at a concentration of about 20 mM to about 75 mM.

10. The pharmaceutical composition of claim 1, wherein the buffer is present at a concentration of about 40 mM to about 50 mM.

11. The pharmaceutical composition of claim 1, wherein the buffer comprises a citrate buffer.

12. The pharmaceutical composition of claim 1, further comprising a chelating agent.

13. The pharmaceutical composition of claim 12, wherein the chelating agent comprises EDTA.

14. The pharmaceutical composition of claim 13, wherein the EDTA is present at a concentration of about 0.005% to about 0.25% weight by volume.

15. The pharmaceutical composition of claim 1, wherein the pharmaceutical composition is shelf-stable for at least about one year under an atmosphere selected from nitrogen, air or a combination thereof, and a temperature of from about 2° C. to about 42° C.

16. A pharmaceutical composition comprising
   a) an active agent comprising N-butyl-deoxynojirimycin, or a pharmaceutically acceptable salt thereof, and
   b) a buffer,
wherein the active agent is present at a concentration of from about 1 mg/mL to about 100 mg/mL and the buffer is present at a concentration of about 20 mM to about 75 mM.

17. The pharmaceutical composition of claim 16, wherein the buffer comprises a citrate buffer.

18. A method for increasing the stability of a formulation comprising an active agent selected from 1-deoxynojirimycin, a pharmaceutically acceptable salt thereof, or a derivative thereof, the method comprising introducing a buffer into the formulation, wherein the active agent is present at a concentration of from about 1 mg/ml to about 100 mg/mL.

19. The method of claim 18, wherein the active agent comprises N-butyl-deoxynojirimycin, or a pharmaceutically acceptable salt thereof.

20. The method of claim 18, wherein the buffer comprises a citrate buffer.

\* \* \* \* \*